United States Patent [19]
Mehdizadeh

[11] Patent Number: 5,895,409
[45] Date of Patent: Apr. 20, 1999

[54] NASAL DILATOR

[76] Inventor: Hamid Mehdizadeh, 14928 Diduca Way, Los Gatos, Calif. 95032

[21] Appl. No.: 08/931,437

[22] Filed: Sep. 16, 1997

[51] Int. Cl.⁶ .................................................. A61M 29/00
[52] U.S. Cl. ........................................ 606/199; 606/204.45
[58] Field of Search ........................... 606/204.45, 199

[56] References Cited

U.S. PATENT DOCUMENTS

| | | |
|---|---|---|
| 3,710,799 | 1/1973 | Caballero .................. 606/199 |
| 4,201,217 | 5/1980 | Slater . |
| 4,414,977 | 11/1983 | Rezakhany .................. 606/199 |
| 5,476,091 | 12/1995 | Johnson . |
| 5,479,944 | 1/1996 | Petruson . |
| 5,533,499 | 7/1996 | Johnson . |
| 5,533,503 | 7/1996 | Doubek et al. . |
| 5,533,506 | 7/1996 | Wood . |
| 5,538,000 | 7/1996 | Rudolph . |

FOREIGN PATENT DOCUMENTS 2631229  5/1989  France ................... 606/199

Primary Examiner—William Lewis

[57] ABSTRACT

A nasal dilator is disclosed which is provided in various sizes to fit and be retained within a person's nostril. The device functions to dilate the nasal passage and allow easier breathing during strenuous exercise, the administration of anesthetics to keep nasal airways open before, during and after general anesthesia which requires ventilation by bag or mouth, or in the presence of some breathing disorders in nasal airways. The dilator in its several embodiments is an open framework of non-toxic, non-abrasive, compliant elongate members which is inserted into the nostril and is retained in place by gentle pressure between the nasal walls and the dilator. Prevention of deep nasal insertion is provided by a larger external end of the dilator which contacts the narrowing nasal passage toward the inner end thereof and also serves as a contact for insertion and removal.

11 Claims, 2 Drawing Sheets

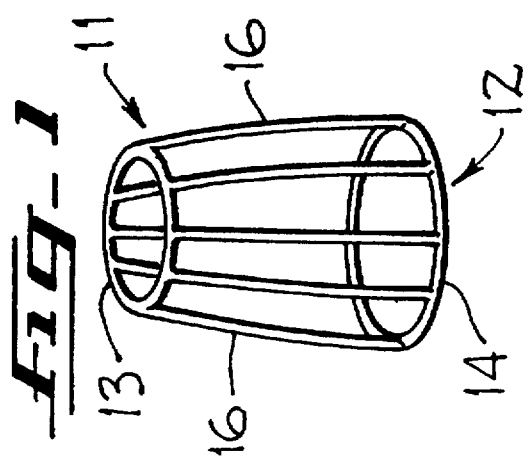
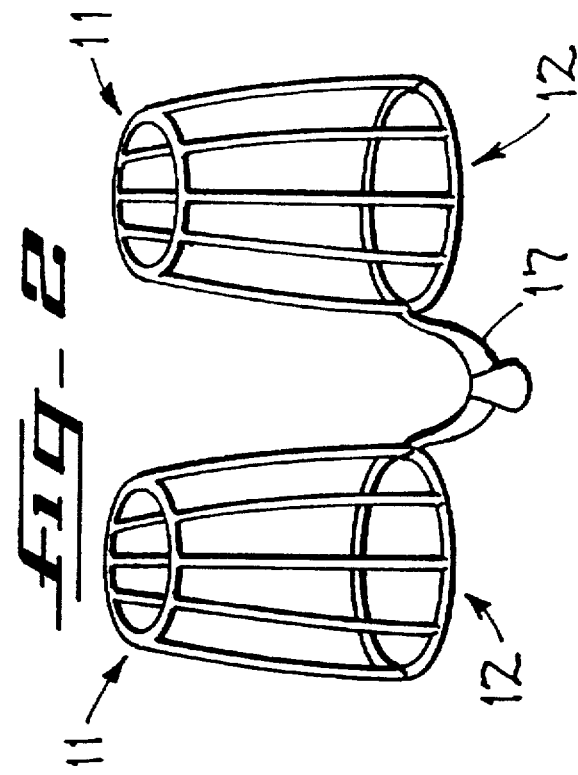
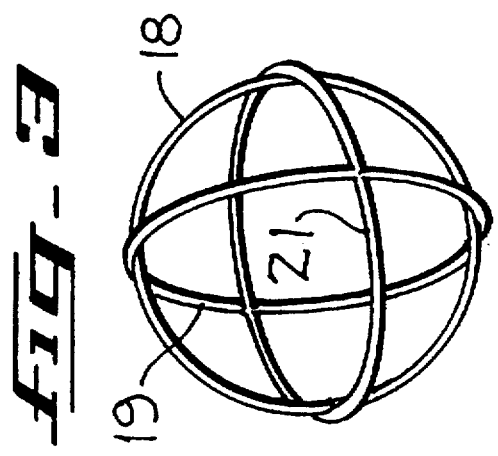
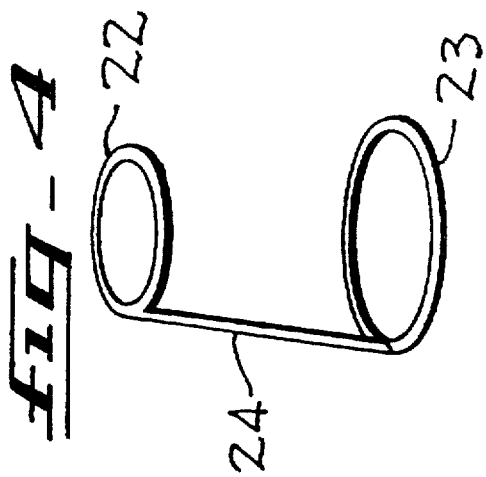

5,895,409

1
NASAL DILATOR

SUMMARY OF THE INVENTION

An open framework is disclosed for positioning internally within and dilating a single nostril, and is constructed from a plurality of interconnected elongate members. The elongate members forming the framework have an interior end and an exterior end. The exterior end is at least as large in cross section as the interior end. The plurality of interconnected members includes at least one convex longitudinal member extending between the interior and the exterior ends.

Further, a nasal dilator is disclosed for internal positioning within a single nostril including an open framework and a plurality of interconnected elongate members within the framework. The plurality of interconnected elongate members are individual continuous loops lying in angularly spaced and intersecting planes.

In yet another aspect of the invention, a nasal dilator is disclosed for internal positioning within a single nostril including an open framework having an interior end and an exterior end and an unobstructed through passage. The through passage includes a smaller opening at the interior end of the framework and a larger opening at the exterior end of the framework. Longitudinal structure extends between the smaller and the larger ends.

DESCRIPTION OF THE DRAWINGS

FIG. 1 is a perspective of one embodiment of the present invention having convex side members.

FIG. 2 is a perspective of a pair of the nasal dilators of FIG. 1.

FIG. 3 is a perspective of a spherical embodiment of the present invention.

FIG. 4 is a perspective of a simplified embodiment of the present invention having a smaller interior end and a larger exterior end.

DESCRIPTION OF THE PREFERRED EMBODIMENTS

Figure 6:
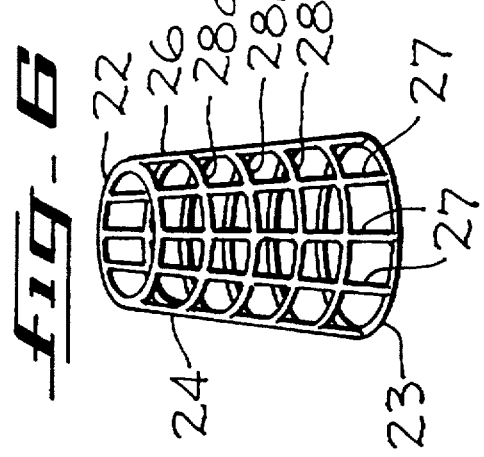
FIG. 6 is a further modification of the embodiment of FIG. 4.

The invention in all of its embodiments described herein is in the form of an open framework with no internal members which would impede airflow. The invention is intended to provide improved breathing capability for persons by expanding the cross section of the nasal passage and thereby increasing the capacity of gas (i.e., air, oxygen, anesthetic, etc.) inhaled by the user. The invention is specifically targeted for persons who experience impeded breathing through the nose or who require a greater intake of air than usual. As aids to deep and increased breathing, these nostril propping devices are designed to be useful inhalation aids in the delivery of inhalant gases such as oxygen or the administration of anesthetic. The invention disclosed herein is also helpful for use by participants in events involving strenuous exertion (i.e., athletic contests) where a larger volume of oxygen intake into the blood stream is required. Further, the disclosed device is useful for alleviating some snoring which occurs when air inhaled through the mouth and throat vibrates relaxed tissue mass in the mouth and throat area. Alleviation of breathing difficulties experienced by asthmatics is also envisioned.

User safety and comfort is anticipated regardless of whether the disclosed device is to be used on a one-time basis or for the long-term. Non-toxic, compliant materials with sufficient elasticity in a bending mode to assist in retaining the devices securely in the nostrils of a user is envisioned. The devices disclosed herein are provided in at least four convenient sizes ranging from small, medium, large to extra large so that they will fit nostril sizes ranging from children to adults. Lengths of the dilator from internal to external ends range from 6 to 18 millimeters. Widest diameters range from 5 to 17 millimeters. It will be noticed that the shapes of the device shown in the drawing figures minimize contact area with the nasal sidewalls and the septum of the nose. The devices shown and disclosed herein are used singly or in pairs as in the embodiment of FIG. 2, wherein a pair of devices is shown connected for use in adjacent nostrils. Any of the embodiments of FIGS. 1 or 3–8 are usable in the paired manner shown in FIG. 2.

With reference now to the drawing FIG. 1 the nasal dilator of the present invention is shown for positioning within a single nostril. An open framework including a plurality of interconnected elongate members is shown having an interior end 11 and an exterior end 12 wherein all of the elongate members lie on the external boundary of the framework. The interior end 11 in FIG. 1 is formed by a smaller loop 13 and the exterior end 12 is formed by a larger loop 14. A number of longitudinal elongate members 16 extend between the loops 13 and 14. The longitudinal members 16 are convex in the embodiment of FIG. 1 and are designed for insertion and retention within the nostril. The larger exterior end 12 is designed to prevent insertion into the nostril beyond a predetermined safe and comfortable distance. The elongate members 13, 14 and 16 are elastic in a bending mode and have an inert, resilient outer surface. The elongate members may have a spring or wire-like core with a soft resilient, low friction, inert outer coating. Alternatively, the elongate members may be cast using a material, such as an inert, low friction plastic, which is itself elastic in bending mode and presents a soft non-abrasive outer surface.

Turning now to FIG. 2, it may be seen that two of the nasal dilators of FIG. 1 are joined by a member 17 so that they may be inserted simultaneously into adjacent nostrils. Various assemblies of the embodiment of FIG. 1 may be presented to fit various sizes of noses. In the same fashion, various sizes of the dilator of FIG. 1 may be provided in the paired embodiment of FIG. 2.

With regard to the embodiment of the nasal dilator shown in FIG. 3, three continuous circular rings 18, 19 and 21 represent the interconnected elongate members. The rings are shown in FIG. 3 as being in substantially orthogonal planes, however the invention described herein envisions the rings being only in spaced relation angularly and in planes which intersect within the framework formed by the members, orthogonality not being essential to the function of the invention. Moreover, the continuous rings 18, 19 and 21 may be elliptical rather than circular and still perform the function of the invention. The diameter of the spherical embodiment shown in FIG. 3, or the embodiment utilizing elliptical rings, envisions a diameter of the device sufficient to comfortably seat within the nostril substantially within the size ranges recited hereinafter.

The embodiment of FIG. 4 is also an open framework and shows a smaller diameter loop 22 at an interior end of a nasal dilator and a larger diameter loop 23 situated at an exterior end of the dilator. The loops 22 and 23 are interconnected by a longitudinal elongate member 24 extending therebetween. The dilator of FIG. 4 is of simplest construction and depends for positioning within the nostril upon appropriately sized rings 22 and 23. As mentioned hereinbefore, insertion distance within the nostril is controlled by the size of the ring 23.

Figure 5:
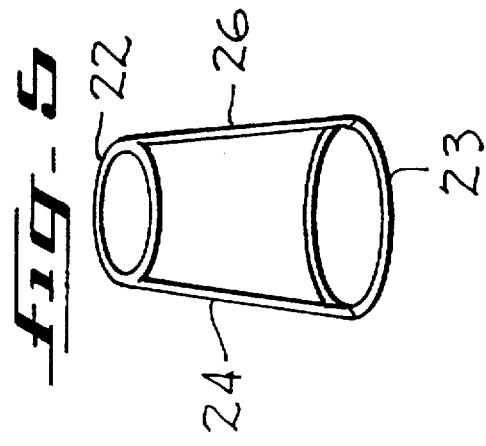
FIG. 5 is a modification of the embodiment of FIG. 4.

As an alternative embodiment to that shown in FIG. 4, the depiction of FIG. 5 includes the ring 22 at the interior end of the dilator and the ring 23 at the exterior end. The longitudinal connecting member 24 is present in FIG. 5 as described with reference to FIG. 4, but an additional longitudinal member 26 is also present, extending between and connected to the interior and exterior rings 22 and 23, respectively. As described in conjunction with the description of previous embodiments, the elongate members 22, 23, 24 and 26 lie on the outer boundary of the framework formed thereby and are fabricated from material which allows elasticity in bending mode and is non-toxic and non-abrasive.

FIG. 6 shows another modification of the embodiment of FIG. 4 wherein additional longitudinal elongate members 27 are attached to and extend between the inner and outer rings 22 and 23, respectively. Further, additional rings graduated in size between the smaller ring 22 and the larger diameter ring 23 are depicted as items 28a, 28b and 28c in the embodiment of FIG. 6.

Figure 7:
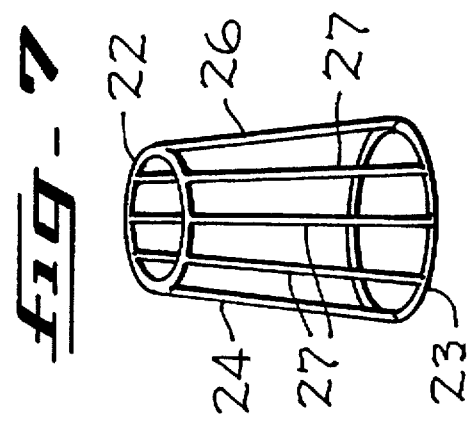
FIG. 7 is yet another modification of the embodiment of FIG. 4.

With reference now to FIG. 7 of the drawings, the smaller diameter ring 22 is situated at the interior end of the nasal dilator and the larger diameter ring 23 is situated at the exterior end. The additional longitudinal elongate members 27 are shown in the embodiment of FIG. 7, but the graduated series of rings 28a–28c are omitted. As described heretofore for the other embodiments of the present invention, the longitudinal elongate members 24, 26 and 27 form an open framework and are fabricated from inert, non-toxic, non-abrasive materials. As also mentioned hereinbefore, the larger diameter ring 23 at the external end of the nasal dilator is configured to prevent uncomfortable or extreme insertion of the dilator into the nostril.

Figure 8:
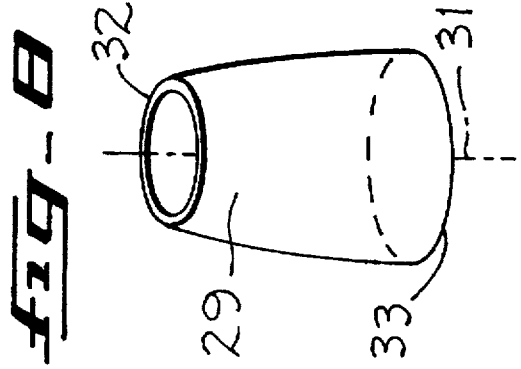
FIG. 8 shows an additional embodiment of the present invention.

FIG. 8 depicts the nasal dilator wherein the open framework has a thin continuous wall 29 surrounding a through passage having a center line 31. The through passage provides an air path. The continuous wall 29 has a convex outside surface for gently engaging the internal surface of the nostril and aiding in retention therewithin. The dilator of FIG. 8 has a smaller internal end 32 and a larger external end 33 to facilitate insertion in a nostril as described hereinbefore.

As discussed in conjunction with all of the foregoing described embodiments of the present invention, the fabrication material from which the elongate members comprising the framework of the dilator are made is non-toxic, non-abrasive and elastic in a bending mode. As a result, the convex longitudinal members in FIGS. 1 and 2 and the convex nature of the members in the embodiment of FIG. 3 engage the walls of the nostril and allow the dilator to remain comfortably in place therewithin. Moreover, the larger ends of the dilators (exterior end 12 in FIGS. 1 and 2 and the ring 23 at the exterior end in FIGS. 4 through 7) engage the nostril wall and prohibit undue insertion within the nasal passage.

The disclosed nasal dilators (except the embodiment of FIG. 8) have been constructed of spring wire 0.5 to 1 millimeter in diameter with a low friction inert coating applied in a process known in the coating industry. Alternatively, the dilators (including the embodiment of FIG. 8) are fabricated using a low friction inert plastic which is elastic in bending mode and cast in the various shapes of the embodiments disclosed herein.

Although the best mode contemplated for carrying out the present invention has been shown and described herein, it will be understood that modification and variation may be made without departing from what is regarded to be the subject matter of the invention.

What is claimed:

1. An open framework for positioning internally within and dilating a single nostril, comprising a plurality of interconnected elongate members forming a nasal passage dilator, said nasal passage dilator having an interior and an exterior end, said exterior end being at least as large as said interior end, said plurality of interconnected elongate members including at least one convex longitudinal member extending between said interior end and said exterior end, further comprising, first, second and third continuous loops interconnected and lying in angularly spaced and intersecting planes.

2. The open framework of claim 1 wherein said first, second and third continuous loops comprise circular loops and wherein said angularly spaced and intersecting planes comprise mutually orthogonal planes.

3. The open framework of claim 1 wherein said plurality of interconnected elongate members comprises first and second elliptical loops interconnected and having major axes extending between said interior end and said exterior end, and a circular loop interconnected with said first and second elliptical loops, said first, second and circular loops lying each in angularly spaced intersecting planes.

4. The open framework of claim 1 wherein said plurality of elongate members comprises, a spring core, and an inert compliant outer coating.

5. The open framework of claim 1 wherein said plurality of interconnected elongate members comprises, an array of inert compliant members elastic in bending mode.

6. An open framework for positioning internally within and dilating a single nostril, comprising a plurality of interconnected elongate members forming a nasal passage dilator, said nasal passage dilator having an interior end and an exterior end, said exterior end being at least as large in cross section as said interior end, said plurality of interconnected members including at least one convex longitudinal member extending between said interior end and said exterior end, a pair of said nasal passage dilators, a connector link extending between said exterior ends of said pair of nasal passage dilators, whereby said pair of nasal passage dilators are spaced apart a distance substantially the same as the distance between a nostril pair and dilation of each of a pair of side by side nostrils is accomplished by insertion therein.

7. The open framework of claim 6 wherein said plurality of interconnected elongate members comprises a spring core, and an inert compliant outer coating.

8. The open framework of claim 6 wherein said plurality of interconnected elongate members comprises an array of compliant members elastic in bending mode.

9. A nasal dilator for internal positioning within a single nostril, comprising an open framework having a plurality of peripheral members surrounding an unobstructed through passage, an interior end on said framework surrounding said through passage, and an exterior end on said open framework surrounding said through passage, said interior end being smaller than and substantially in a plane parallel to said exterior end to facilitate insertion into the nostril, said plurality of peripheral members extending between said interior and exterior ends for contacting and facilitating retention within the nostril.

10. The nasal dilator of claim 5 wherein said plurality of peripheral members comprises an array of compliant convex members elastic in bending mode.

11. The nasal dilator of claim 5 wherein said plurality of peripheral members comprises a continuous convex wall extending between said interior and exterior ends for facilitating retention in the nostril.

* * * * *